United States Patent [19]

Denkinger

[11] 4,037,601
[45] July 26, 1977

[54] PROCESS FOR PREPARING STERILIZED FEMININE HYGIENE ARTICLES OF NON-WOVEN AND WOVEN TEXTURES

[76] Inventor: Marian C. Denkinger, 88-35 Elmhurst Ave., Elmhurst, N.Y. 11373

[21] Appl. No.: 681,798

[22] Filed: Apr. 30, 1976

[51] Int. Cl.² .......................... A61F 13/00; A61F 5/46
[52] U.S. Cl. .................................... 128/285; 128/270; 128/271
[58] Field of Search ............... 128/270, 285, 271, 263, 128/130, 157, 290 P, 217

[56] References Cited
U.S. PATENT DOCUMENTS

| 61,417 | 1/1867 | Grant | 128/285 |
| 183,388 | 10/1876 | Fowler et al. | 128/271 |
| 1,876,703 | 9/1932 | Lilly | 128/271 |
| 2,333,342 | 11/1943 | Slocumb | 128/271 |
| 3,342,181 | 9/1967 | Jacquignon | 128/260 |
| 3,763,861 | 10/1973 | Forti et al. | 128/271 |
| 3,905,372 | 9/1975 | Denkinger | 128/285 |

Primary Examiner—Aldrich F. Medberry

[57] ABSTRACT

A process for preparing sterilized hot melt adhesive bonded articles is disclosed comprising applying to one surface of an adhesive, such as a hot melt adhesive film, a blend of polypropylene, a tackifying hydrocarbon resin, and a diluent, pressing the surfaces onto the adhesive while it is molten, and subsequently thermally sterilizing the bonded article.

4 Claims, 4 Drawing Figures

PROCESS FOR PREPARING STERILIZED FEMININE HYGIENE ARTICLES OF NON-WOVEN AND WOVEN TEXTURES

BACKGROUND

This invention relates to thermally sterilized articles bonded to hot melt adhesives and more particularly to such articles bonded with a hot melt adhesive based on polypropylene.

Disposable hygiene products are used extensively by women and hospitals. It is necessary that such disposable articles be sterile. Also, for reasons of economy, it is necessary that such articles be cheap, very convenient method of forming such articles is by the use of a hot melt adhesive which is applied molten to one surface of a forming mold. The surfaces of the mold are then pressed together with non-woven or woven fabric therebetween, and a shaping bond forms as the adhesive cools. This method of forming is particularly useful in the manufacture of shaped hygiene products made from non-woven fabrics. Special hot melt adhesives useful to meet the resoftening are viscous and can be applied easily, and can be applied discontinuously to form an interrupted surface.

I have found that hot melt bonded article capable of withstanding thermal sterilization can be prepared by the technique of bonding with hot melt adhesives using an adhesive comprising a blend of polypropylene, containing a tackifying resin, and a wax diluent.

SUMMARY

It is an object of this invention to provide a method for preparing sterilized feminine hygiene articles bonded with hot melt adhesives.

A further object is to provide thermally sterilized articles having one face bonded with a hot melt adhesive.

More specifically, in accordance with this invention a sterilized, hot melt bonded feminine article is prepared by applying to a surface a hot melt adhesive comprising:

1. a blend of polypropylene;
2. a tackifying resin, selected from the group consisting of polyterpene resins, and petroleum hydrocarbon resins an hydrogenated petroleum hydrocarbon resins having a softening point between 50° C and 200° C, and;
3. a diluent selected from the group consisting of petroleum waxes, Fischer-Tropsch wax, wax grade polyethylene, plastic grade polyethylene having a melt index at least 40, applying it in a continuous or discontinuous film over a mold, the mold having male projections thereon, pressing the female surfaces of the mold over the male surfaces together, while the adhesive is molten, with a non-woven or woven fabric therebetween and subsequently sterilizing the bond and substrate by heating.

The ratio of polypropylene to tackifying resin should between 1:1 and 10:1. The adhesive composition may include up to about 50 percent by weight of the diluent.

PREFERRED EMBODIMENTS

The polypropylene of the adhesive used in the process of this invention is an "atactic" polymer because the configurations of the repeating units in its chain vary in the random manner along the chain, with softening point of 100°-160° C. Useful polypropylene blends will typically have a ball and ring softening point, as determined by ASTM method E 28-58T, of about 90° C to about 100° C; a molten viscosity of about 800 centipoises to about 18,000 centipoises at 350° F, as measured with a Brookfield Viscometer, using a No. 6 spindle, at 20 revolutions per minute; and a specific gravity of from about 0.75 to about 0.90.

The tackifying resin component of the hot melt adhesive is added to develop the adhesive stickiness, plasticity, and wetting ability, and to modify the viscosity of the adhesive. Suitable resins are hydrocarbon resins having a ball and ring softening point between about 70° C and about 150° C, e.g., the petroleum hydrocarbon resins, hydrogenated petroleum hydrocarbon resins, polyterpene resins, and synthetic aliphatic hydrocarbon resins, having the required softening points.

It is desirable to include a diluent in the hot melt adhesive to reduce the melt viscosity or alter cohesive characteristics of the hot melt adhesive composition without decreasing its binding characteristics. Such diluents may be petroleum waxes, Fischer-Tropsch waxes, wax grade polyethylene, and plastic grade polyethylene having a melt index of at least 50.

The polypropylene constituent of the hot melt adhesive should be present in a minimum concentration of 20 percent, by weight. The weight ratio of polypropylene to tackifying resin should range from about 1:1 to 10:1. Weight ratios below 1:1 give adhesive film which is excessively waxy and lacks proper tackiness. Adhesives having low concentrations of tackifying resin also show relatively poor elevated temperature aging properties.

While I have talked in terms of a feminine hygiene article formed on a film of a hot melt adhesive, this is one possibility. Organic plastisol plastic latices of any synthetic resins, and one possibility, rubber latex is another. In the manufacture of the contraceptive sheath, which commonly is used by the male there is the perfect form for use. The form is dipped in rubber latex, but prior to the vulcanization of the latex, it is dusted with non-woven fiber, or actually the non-woven fiber or even a woven fiber is formed thereover by means of a female mold matching the male mold. Thereafter, the latex is vulcanized. The rubber particles contact some of the fibers, enough of the fibers in the material to form a film giving it a form which makes it of optimum utility. Any of the latex formulations and vulcanization operations useful for the formation of the contraceptive sheaths are to be considered useful herein.

Similarly, to give the non-woven fabric or the woven fabric a form approximating that of the hygiene produce and using again the mold with the male projections thereof, it is possible to use a starch gelatin to form a film thereover. The starch, generally laundry grade, can be formed as a solution of collidal suspension, sprayed over the mold in sufficient quantity to form at least a discontinuous film over the mold and thereafter the mold used to shape the non-woven fabric or the woven fabric used to the form desired. The starch has the advantage that while it will be a bit firm in the dry stage, it permits the handling of these objects, gives them a form useful for the purpose of packaging. When they are inserted into the vaginal canal of the woman using this material, the form of the starch is quickly softened by the moisture normally present there, so that the product becomes quite comfortable. The starch has the advantage that it is totally compatible with the tissue and no side reactions can be expected therefrom.

The use of the hot melt adhesive formulations or the rubber adhesive, where they are to be in contact with the moist tissue for hours at a time has to be recommended with the precautionary note that some recipients of these materials may be recommended with the precautionary note that some recipients of these materials may be sensitive to them and develop side reactions. This is not the case with starch.

In may U.S. Pat. No. 3,905,372, issued Sept. 16, 1975, which is to be considered fully incorporated herein, I have illustrated an optimum or several forms of the feminine hygiene article.

In the formation of these articles in accordance with this invention, using either a hot melt adhesive, starch or rubber, the method is better understood by reference to the drawings, wherein.

Figure 1:
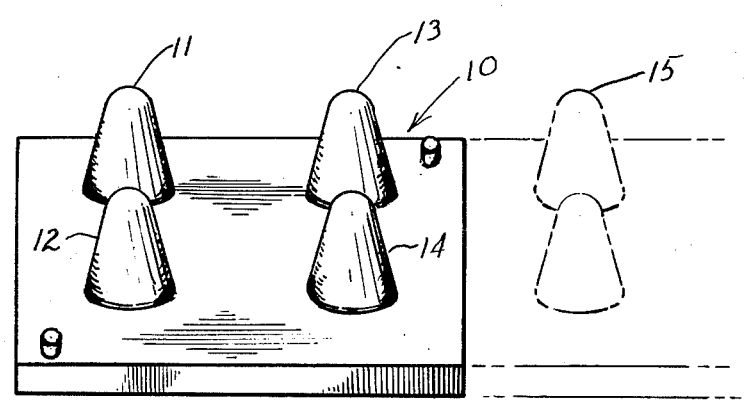
FIG. 1 is a perspective view of a small mold corresponding to the male portion of the mold, in the terminology which I have adopted.
Figure 3:
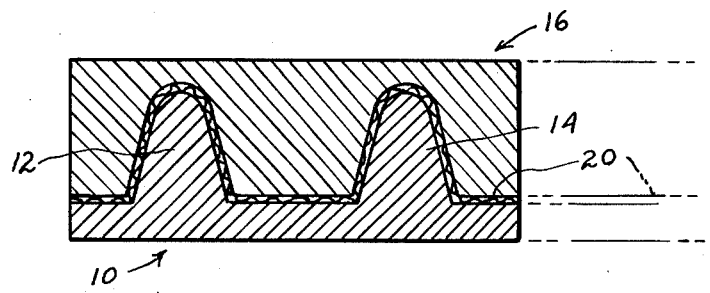
FIG. 3 illustrates the formation of the article.

In FIG. 1, 10 is the base of the mold which is merely a flat metal, or can be actually a plastic, high melt grade, thermoset, and the base is provided with a sequence of projections, male form, 11, 12, 13, 14 and 15, as shown herein, to set the size and shape desired of the final product. Generally, these will be small and perhaps no larger in diameter than a user's forefinger or middle finger, which is considered the optimum insertion tool.

Figure 2:
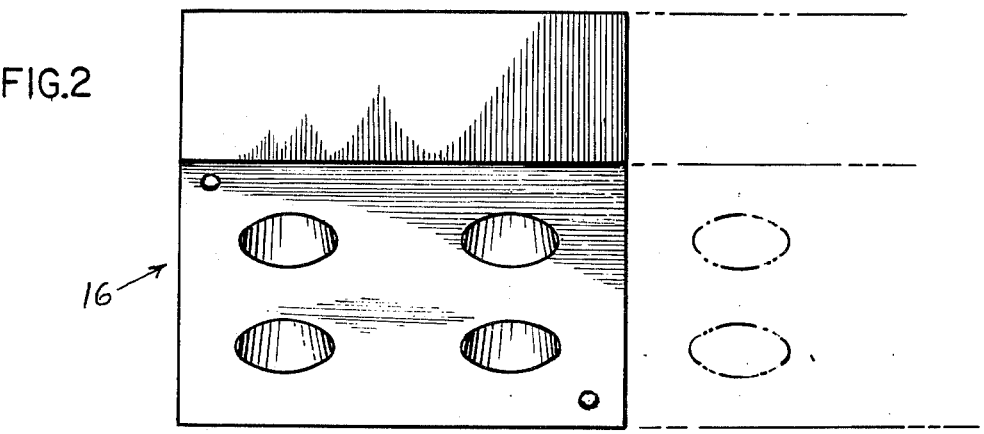
FIG. 2 is the female mold.

The female mold, shown in FIG. 2, as the terminology indicates, is the mirror image of the male mold.

The process of manufacture thus consists of coating the male mold with a continuous or even a discontinuous film of the adhesive to be used. If it is a hot melt adhesive, the mold must be heated sufficiently to keep the adhesive in molten tacky condition. If rubber latex is used, there is no significant heating problem, because the latex itself is stable, liquid, and forms a film rather easily. Starch, similarly, in aqueous suspension colloidal suspension, such as used in laundry, can be sprayed in place to form a relatively continuous or discontinuous film, and thus, it is perhaps the cheapest and most conveniently used adhesive. Having applied the film to the male mold, a sheet of non-woven textile fabric, 20, is dropped over the male mold. The female mold, 16, is pressed into place, the combination heated or warmed to set the adhesive, separated, and the formed articles are then peeled free to give a product looking like that in FIG. 4, which is the formed textile fabric. Individual items are obtained by cutting these apart along the base. The process is thus useful for forming the shaped article together with the lip or face, which is useful.

Where the adhesive is a rubber latex, an additional step is involved, in that having pressed the fabric, non-woven, or woven, into place, to cause at one face of it to be imbedded in the adhesive the combination is passed into a vulcanizing-warming chamber to set the rubber latex.

It should be apparent that the principal function of the adhesive in this method is to give shape to the article, sufficient to allow it to be packed conveniently and allow it to be inserted conveniently. The firmness of the adhesive should be such that the article collapses under pressure, such as it encounters in the vaginal canal, and actually creates no sensation of discomfort through any harshness or stiffness in it. The hot melt adhesive thus is used very sparingly, barely sufficient to form a film to engage the inner surface of the molded fabric material.

The rubber latex can be used more freely, because it is inherently flexible and forms a discontinuous film readily when it is molded in the mechanism here. That is, the coating of the male mold with a non-woven or woven fabric, or even loose fibers to form what is effectively a condom with a furry or fibrous exterior given a structure which is continuous rubber film with the fibers thereon.

The starch, similarly, provides what may seem like a relatively stiff object at first, but as soon as it contacts body moisture, it collapses and is quite a comfortable article.

The hot melt adhesives are prepared in conventional manner, by placing the hydrocarbon tackifying resin in a mixing kettle, equipped with rotors, and raising the temperature to a range of from about 225° F to 450° F, the exact temperature depending on the melting point of the tackifying resin and polypropylene. When resin has melted, stirring is initiated and the polypropylene is added. Stirring and heating are continued until a smooth, homogeneous mass is obtained. The optional ingredients are then added and thoroughly blended. The resulting hot melt adhesive composition is drawn off and may be used immediately in hot pots, or it may be molten-extruded into rope form and converted into pellets, rods, cylinders, slugs, or slats depending on the equipment which will subsequently be used to apply it. The adhesive may also be placed in cooling pans and held in bulk form for later use, or it may be granulated or diced.

After the feminine hygiene articles are molded they are sterilized by heating to a temperature of 200° F to 300° F in any conventional oven.

The invention will be further illustrated by the following examples of hot melts, useful for my purposes, which are not, however, intended to limit its scope:

EXAMPLE I

A hot melt adhesive was prepared by having the following composition:

| | |
|---|---|
| Polypropylene Ball and ring sofening point 320° F | 50 parts by weight |
| Petroleum hydrocarbon resin Ball and ring softening point 120° F | 50 parts by weight |

The adhesive showed viscosity of about 130 centipoises at 350° F.

Bonds made with non-woven fabrics using my method of molding remained strong after a thermal sterilization treatment. It is a product developed in definite form with the hot melt adhesive giving it its form.

Typical useful hot melt formulations can be found in the following:

U.S. Pat. No. 3,577,372: Flanagan
U.S. Pat. No. 3,341,626: Peterkin
U.S. Pat. No. 3,492,372: Flanagan
U.S. Pat. No. 3,356,766: Ware
U.S. Pat. No. 3,634,546: Hagemeyer
U.S. Pat. No. 3,700,758: Johnson et al
U.S. Pat. No. 3,370,106: Hall et al
U.S. Pat. No. 3,684,643: Stepp
U.S. Pat. No. 3,798,118: Jones In further recapitulation, in addition to the variety of adhesives which can be used, it should be noted that as fibrous materials I can use cotton, cellulose, mixed cotton and cellulose (including tissue paper), formed as a bat which is molded around the form, as well as non-woven fibers and woven materials of a gauze like texture. In general, the test of adequacy is that the fibers be soft, absorbent and cheap.

Figure 4:
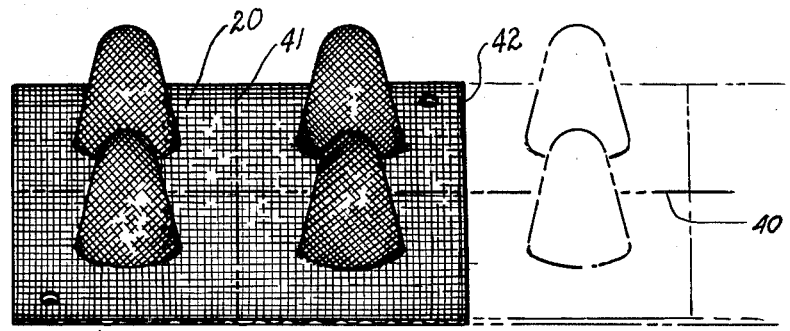
FIG. 4 illustrates the formed article.

In FIG. 4 I illustrate a sheet of the articles as lifted from the mold. It is apparent that by cutting along lines 40, 41, 42, etc., the individual articles are separated. The flat portion, or apron, thus attached to each article, provides a tab.

What is claimed is:

1. A feminine hygiene product for digital insertion into the vaginal canal having the following characteristics:
   a fundamentally hollow form defined by an outer convex surface of fibrous absorbent textile material,
   an inner surface formed of a film of a material selected from the group consisting of hot melt adhesive, rubber latex, synthetic plastisol latex and starch,
   said film being adhered to and received in its outer convex surface, fibers of said textile material, thereby to give said product a unitary conical form defining a flexible digital receiving liner and an exterior fibrous surface for vaginal conal contact.

2. Product in accordance with claim 1, in which the exterior fibrous surface is formed of absorbent non-woven fabric.

3. The method of forming a feminine hygiene article suitable for insertion into the vaginal canal, using a finger as the insertion tool, comprising a hollow, somewhat conical shape article
   having its inner surface defined by a film of a plastic material and its outer surface defined by a layer of absorbent material,
   the method consisting of the steps of coating a properly shaped die with the plastic material, suitable for forming the liner,
   applying to said coated die fibrous material suitable for forming the absorbent exterior,
   causing said fibrous material partially to enter and be held by the adhesive film and
   thereafter causing the film to set, and subsequently removing said article from the die.

4. A product in accordance with claim 1 in which the exterior surface is formed of absorbent woven fabric.

* * * * *